(12) United States Patent
Grellmann et al.

(10) Patent No.: US 7,246,264 B2
(45) Date of Patent: Jul. 17, 2007

(54) REMOTE ULTRASOUND SYSTEM DIAGNOSTICS

(75) Inventors: Reinhold G. Grellmann, Snohomish, WA (US); Daniel M. McCabe, Snohomish, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 749 days.

(21) Appl. No.: 10/713,600

(22) Filed: Nov. 13, 2003

(65) Prior Publication Data

US 2004/0153862 A1 Aug. 5, 2004

Related U.S. Application Data

(63) Continuation of application No. 09/534,143, filed on Mar. 23, 2000, now abandoned.

(51) Int. Cl.
*G06F 11/00* (2006.01)
(52) U.S. Cl. ....................................................... 714/25
(58) Field of Classification Search .................. 714/25
See application file for complete search history.

(56) References Cited

U.S. PATENT DOCUMENTS

| 5,107,499 | A | 4/1992 | Lirov et al. |
|---|---|---|---|
| 5,195,095 | A | 3/1993 | Shah |
| 5,491,791 | A | 2/1996 | Glowny et al. |
| 5,517,994 | A | 5/1996 | Burke et al. |
| 5,603,323 | A | 2/1997 | Pflugrath et al. |
| 5,715,823 | A | 2/1998 | Wood et al. |
| 5,812,397 | A * | 9/1998 | Pech et al. .................... 700/81 |
| 5,851,186 | A | 12/1998 | Wood et al. |
| 5,907,617 | A | 5/1999 | Ronning |
| 6,009,401 | A | 12/1999 | Horstmann |
| 6,298,454 | B1 | 10/2001 | Schleiss et al. |
| 6,350,239 | B1 | 2/2002 | Ohad et al. |
| 6,353,445 | B1 | 3/2002 | Babula et al. |
| 6,377,162 | B1 | 4/2002 | Delestienne et al. |
| 6,381,557 | B1 | 4/2002 | Babula et al. |
| 6,440,072 | B1 | 8/2002 | Schuman et al. |
| 6,490,684 | B1 | 12/2002 | Fenstemaker et al. |

FOREIGN PATENT DOCUMENTS

| EP | 0 844 581 | 5/1998 |
|---|---|---|
| EP | 0 896 287 | 2/1999 |
| WO | WO 99/32031 | 7/1999 |
| WO | PCT/EP 01/02996 | 4/2002 |

* cited by examiner

*Primary Examiner*—Michael Maskulinski
(74) *Attorney, Agent, or Firm*—Brinton Yorks, Jr.

(57) ABSTRACT

A remote diagnostics system for an ultrasound system is described comprising a laptop computer for a serviceperson which can diagnose, test, modify or upgrade an ultrasound system either on-site or from a remote location. Diagnostic information obtained by the laptop computer is thereafter uploaded to the manufacturer where the information is used to understand and repair error conditions and to design future products.

7 Claims, 9 Drawing Sheets

Remote Diagnostics Mode

This system is being serviced remotely and is unavailable for normal use. Please contact your local service representative before using this system.

REMOTE ULTRASOUND SYSTEM DIAGNOSTICS

This application is a continuation of application Ser. No. 09/534,143, filed Mar. 23, 2000 now abandoned.

This invention relates to ultrasonic diagnostic imaging systems and, in particular, to ultrasonic diagnostic imaging systems which can be remotely queried, diagnosed, and upgraded.

U.S. Pat. No. 5,603,323 describes methods and apparatus for communicating with a medical diagnostic ultrasound system from a remote location. As described in this patent, an ultrasound system manufacturer or maintenance center can remotely connect to an ultrasound system over a network for the purposes of obtaining information about the ultrasound system's operation and remotely installing software for new features and system performance upgrades. U.S. Pat. No. 5,715,823 expands on these principles and illustrates connections to an ultrasound system by way of the Internet. This patent also describes the remote access to system diagnostic and error logs, and remotely controlled operation of an ultrasound system.

The present invention expands further on these concepts and describes apparatus and techniques by which a serviceperson can comprehensively diagnose and upgrade an ultrasound system from a remote location by means of a diagnostic computer such as a laptop computer. In accordance with the principles of the present invention, diagnostic information can be remotely acquired from an ultrasound system and automatically forwarded to a central diagnostics center for analysis and product quality enhancement. The ultrasound system can be tested from the remote location and both hardware and software can be modified and upgraded. The owner or user of the ultrasound system is notified when these procedures are underway and completed. Software files on the ultrasound system can be remotely repaired, and new features can be remotely activated for either temporary or permanent use.

Figure 1:
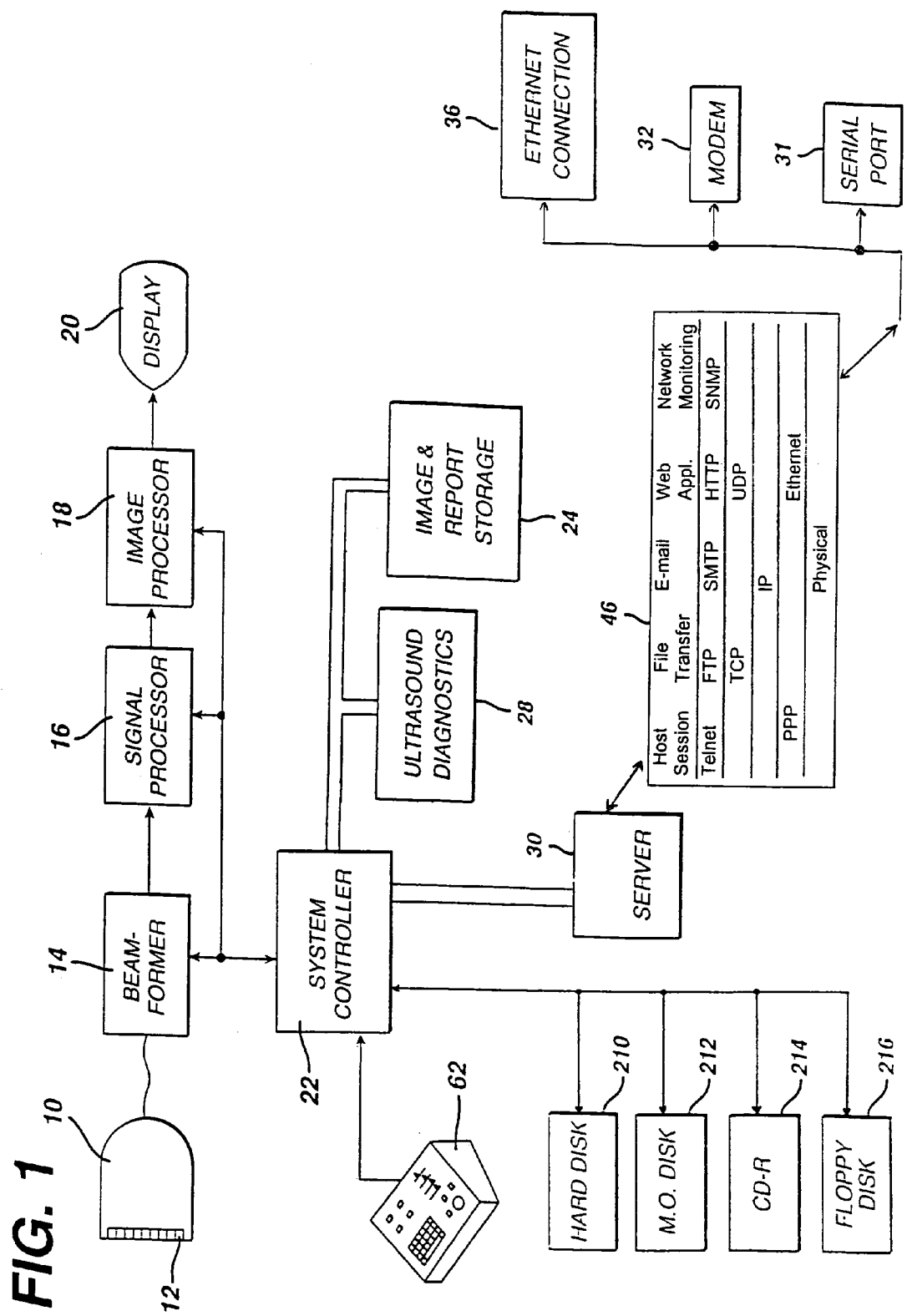
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. At the top of the drawing is the signal path of a typical ultrasound system, including a probe 10 with an array transducer 12 which transmits and receives ultrasound signals, a beam former 14 which processes the signals from the elements of the array transducer to form coherent echo signals, an ultrasound signal processor 16, an image processor 18, and a display 20 on which the ultrasound image and data are displayed. The operation of these components is coordinated by a system controller 22. The operation of the ultrasound system is directed by user controls 62 coupled to the system controller. The system controller 22 can store images and diagnostic reports on storage device 24. The system controller also has access to ultrasound diagnostics 28 for the performance of diagnostic tests and maintenance of the ultrasound system.

The ultrasound system includes a number of devices for the storage and communication of data, such as a hard disk 210, a magneto-optical disk 212, a CD-R drive 214, and a floppy disk 216. Some or all of the capacity for the image and report storage 24 and for storing ultrasound diagnostics 28 may be provided by these devices. The ultrasound system can also send and receive information from external sources by way of a server 30. The server communicates through a stack of protocols 46, which illustrates some of the more universal communications protocols which may be employed. At the upper layer of the stack 46 are applications protocols for host sessions, file transfer, e-mail, Web applications and network monitoring. At the next level of the stack are Telnet, FTP, SMTP, HTTP and SNMP presentation protocols. At the third layer are the TCP and UDP protocols, and at the next layer is the IP protocol. At the fifth layer are PPP and Ethernet protocols, and at the bottom of the stack is the physical layer which connects to external communication devices. Several communication devices are shown in the embodiment of FIG. 1, including a serial port 31, a modem 32, and a network (Ethernet) connection 36. This array of communication protocols enables the ultrasound system to connect to directly connected devices, by way of proprietary or public point-to-point networks, by phone lines, and/or over the Internet and the World Wide Web.

Figure 2:
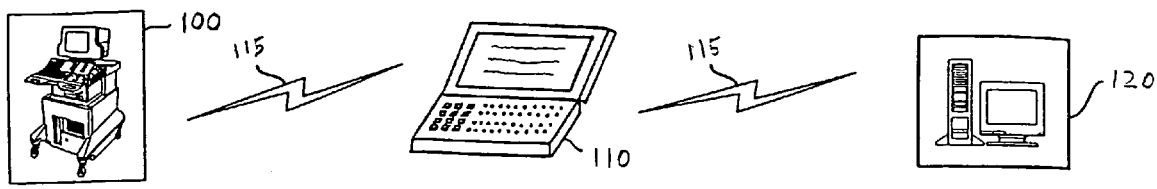
FIGS. 2-2d illustrate communication connections between an ultrasound system, a portable diagnostic system, and a central diagnostics center.

The ultrasound system of FIG. 1 can be remotely diagnosed and modified over a network as shown in FIG. 2. In a preferred embodiment an ultrasound system 100 is diagnosed and modified or upgraded by diagnostic programs resident on a portable diagnostic system such as a laptop computer 110. While diagnostic routines can be stored on and operated from a desktop PC or other computer as described in the aforementioned patents, a laptop computer is advantageous because it can be carried by a serviceperson and used to diagnose the ultrasound system 100 either at the location of the ultrasound system or from a remote location over a phone line or other network 115. The present invention encompasses diagnosis from laptop computers, desktop computers, specially designed diagnostic instruments, central computer stations, and other database systems and networks. These diagnostic devices preferably all include communication protocols necessary to communicate with those utilized in the ultrasound system, for instance, those shown in protocol stack 46. In a preferred embodiment the laptop computer 110 can be remotely connected to a central diagnostics center 120 such as the service dispatch center, factory, or other location with which a serviceperson communicates over a network 115 so that diagnostic information acquired by the serviceperson can be transferred to the diagnostics center 120 for further technical and statistical analysis as described below. The diagnostics center 120 can also provide new or improved diagnostic software to the laptop computer over the network 115, as well as other useful information (e.g., service call information) for the serviceperson.

Figure 2A:
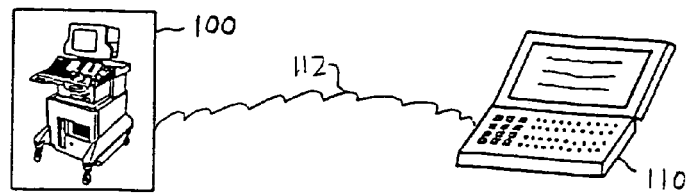
Figure 2B:
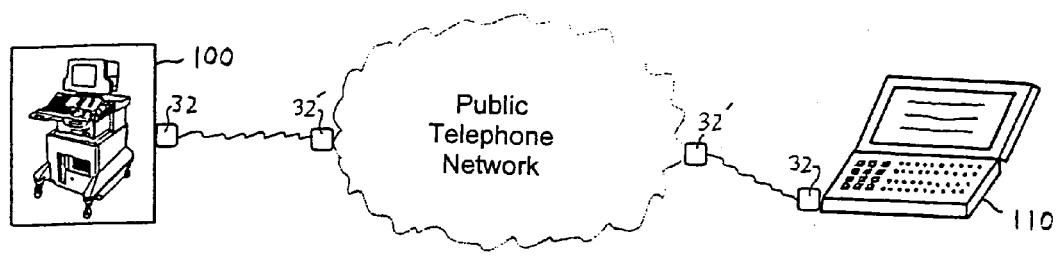

Various connections which are possible among the ultrasound system 100, the laptop computer 110, and the diagnostics center 120 are shown in FIGS. 2a-2d. FIG. 2a illustrates a local serial connection which may be used when the diagnostic laptop computer 110 is at the site of the ultrasound system 100. This drawing shows a serial/PPP connection between the laptop computer 110 and the ultrasound system 100. FIG. 2b illustrates a dial-in connection between the laptop computer 110 and the ultrasound system 100, which may be used when the laptop computer is at a location remote from that of the ultrasound system. In this case a serial/PPP connection is made by way of a public telephone network through modems 32 of the laptop computer 110 and the ultrasound system 100 and modems or modem-compatible circuitry 32' of the telephone network.

Figure 2C:
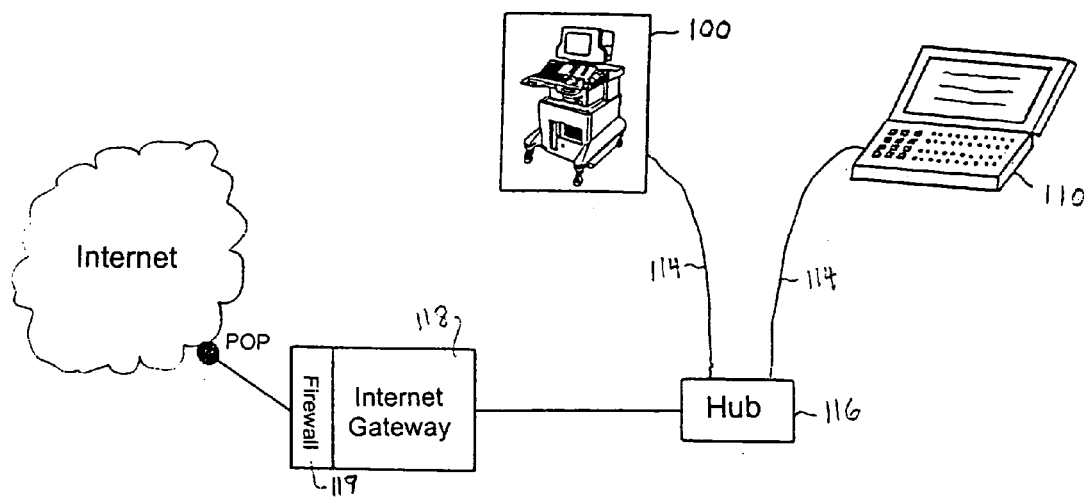

FIG. 2c illustrates a local network connection between the laptop computer 110 and the ultrasound system 100. In this case the laptop computer 110 and the ultrasound system both have network connections (e.g., Ethernet) to a network hub 116 which puts them in communication with each other. This drawing also illustrates the connection of the network to the Internet by an Internet gateway 118 having a firewall 119 by which the gateway is connected to a point of presence (POP) on the Internet. Hence a diagnostic laptop computer can also access the ultrasound system via the network by connecting to the Internet.

Figure 2D:
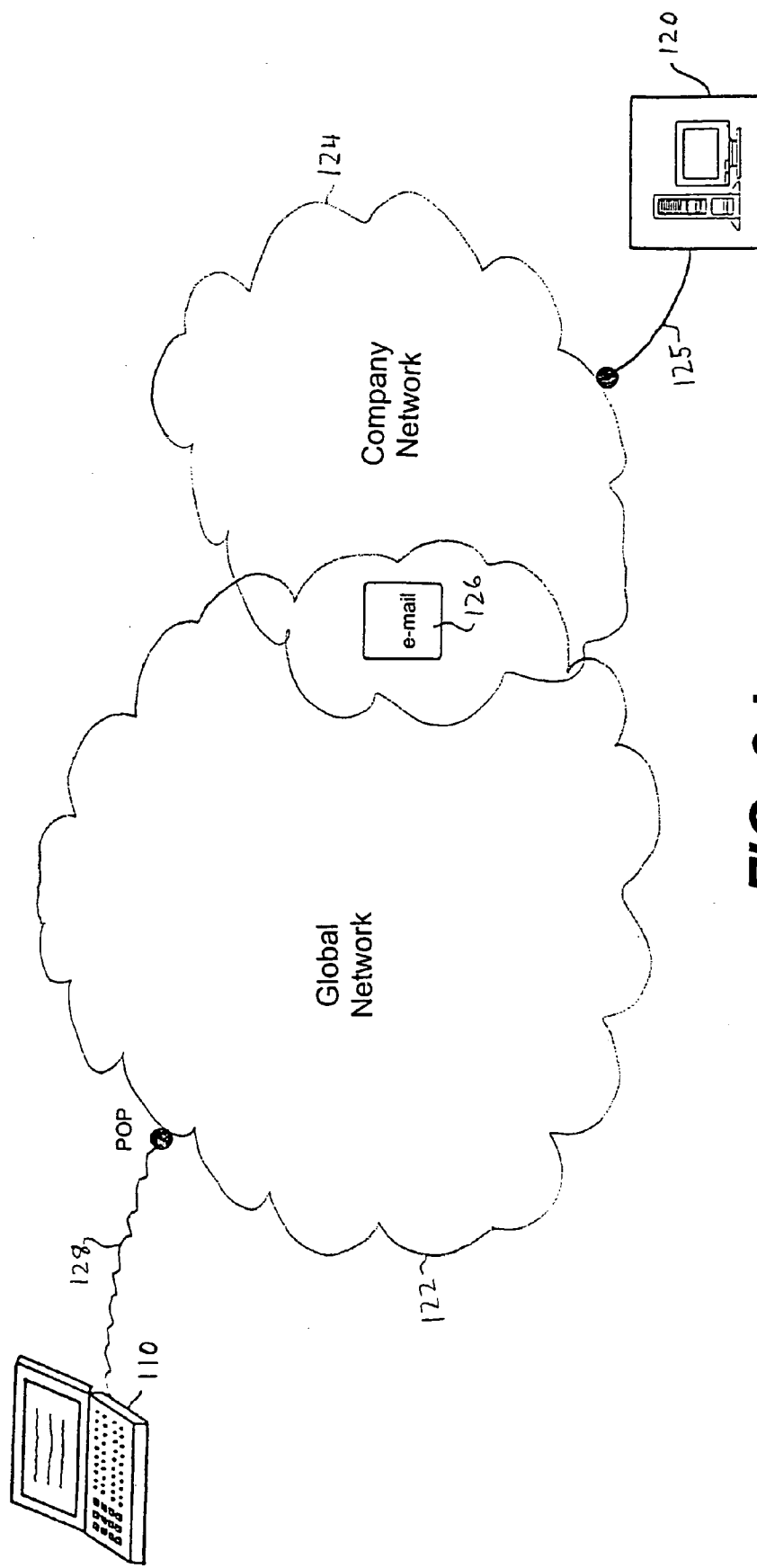

In a constructed embodiment of the present invention the diagnostic laptop computers used to diagnose ultrasound systems can connect to the central diagnostics center 120 from anywhere in the world over a global network as shown in FIG. 2d. In this drawing a laptop computer 110 connects to the global network 122 by a serial PPP connection 128. A company network 124 associated with the ultrasound system manufacturer is connected to the global network. The company network includes one or more e-mail servers 126 connected to the global network which facilitate the transmission of ultrasound system diagnostic data to the diagnostic center by e-mail. The diagnostic data can also be transferred directly to the diagnostic center's servers, workstations, PCs or laptop computers on the company network 124 by file transfer protocols. These devices are directly connected to the company network 124 by network connections 125.

Figure 3:
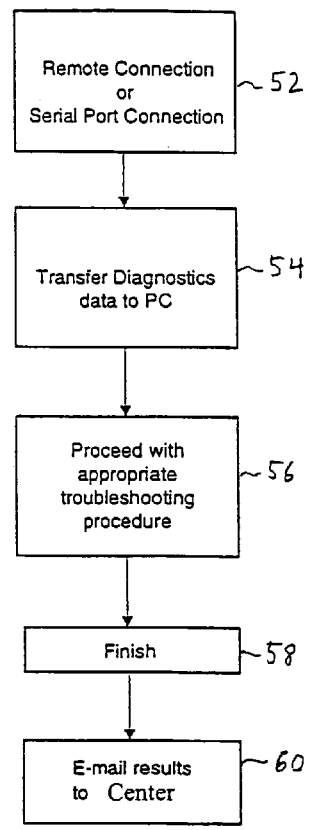
FIG. 3 is a flowchart of procedures for diagnosing an ultrasound system in accordance with the present invention.

FIG. 3 illustrates a process by which the laptop computer 110 can be used to diagnose the ultrasound system 100. The laptop computer first (52) establishes a network connection with the ultrasound system when remotely located from the ultrasound system. This can be done by modem connection to the modem 32 in the ultrasound system, or by connecting to the network to which the ultrasound system's Ethernet connection is connected. When the serviceperson is at the site of the ultrasound system the connection can be made directly to the serial port 34 of the ultrasound system. The laptop computer contains communication software and hardware (e.g., server software, FTP, TCP/IP, PPP, modem, Ethernet, Internet, etc.) which is compatible with any of the connectivity capabilities of the ultrasound system such as those shown at 30-46 in FIG. 1. Once communication has been established between the diagnostic computer and the ultrasound system, the diagnostic data in the ultrasound system is downloaded to the diagnostic computer (54), several examples of which are described below. From a review of the diagnostic data downloaded to the laptop computer, the serviceperson performs the required troubleshooting and repair or modification of the ultrasound system (56). When the serviceperson has completed the testing, repairs, upgrading or diagnosis the connection to the ultrasound system is disconnected (58). Thereafter the diagnostic data and results of the testing, diagnosis, upgrades or repair can be electronically sent to the central diagnostics center 120 (60).

Figure 4:
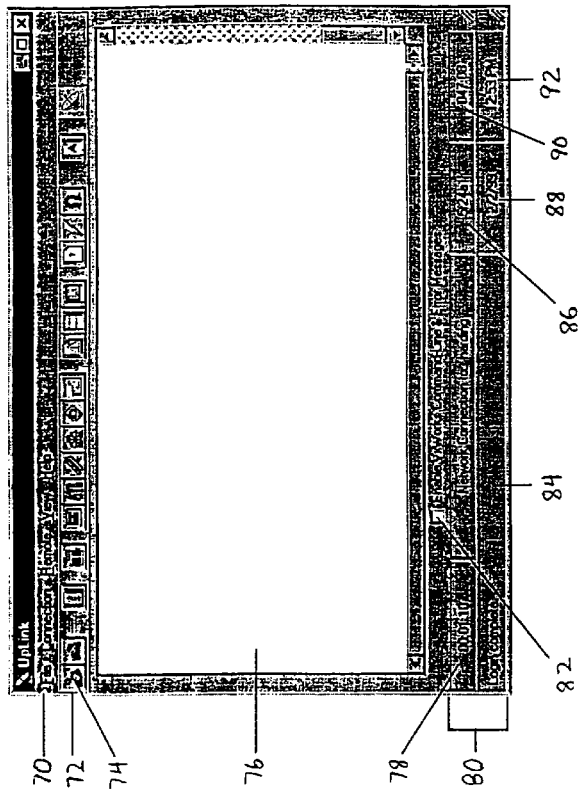
FIG. 4 illustrates the display screen of a diagnostics computer constructed in accordance with the principles of the present invention.

FIG. 4 illustrates the display screen of a constructed embodiment of the present invention. At the top of the screen at 70 are menus which the serviceperson can use to control and operate the diagnostic system on the laptop computer. Below the menus is a toolbar 72 for performing specific diagnostic functions as described below. The first button 74 of the toolbar is the Connect button, which is activated to connect the diagnostic computer to the ultrasound system. In the center of the screen is a text window 76. Below the text window is a timer display 78 of the duration of a remote connection to an ultrasound system. The timer display 78 is one of the connection status displays 80, which also include a status bar 84 that displays the current status of the connection. The identification of the ultrasound system to which the connection is made is displayed at 86, and the software version of the ultrasound system is displayed at 90. A command line check box 82 can be checked when the serviceperson desires to control the diagnostic procedure with text commands in the text window 76. When the check box 82 is not checked, the diagnostic computer operates automatically through menu commands and the buttons in the toolbar 72. The date and time are shown at 88 and 92.

Figure 5:
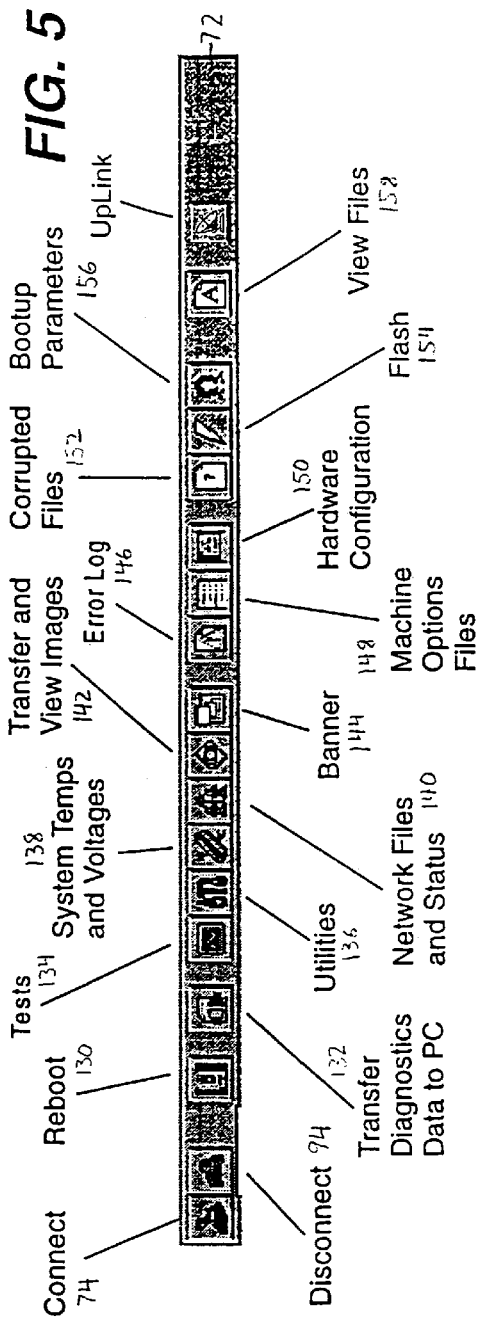
FIG. 5 illustrates the toolbar of the display screen of FIG. 4 in greater detail.
Figure 6:
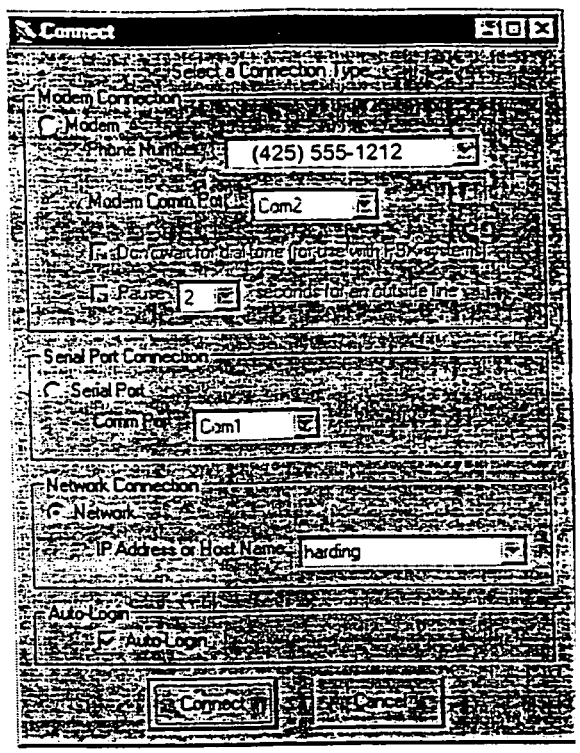
FIG. 6 illustrates a display screen for connecting a diagnostics computer to an ultrasound system.

To connect the laptop computer to an ultrasound system, the serviceperson clicks on the Connect button 74, shown in the enlarged view of the toolbar in FIG. 5. Clicking the Connect button brings up the Connect screen shown in FIG. 6. The Connect screen presents a choice of modem connection, serial port connection or a network connection to the ultrasound system. For a serial port connection to the ultrasound system, which is frequently used when the serviceperson is at the ultrasound system site, the serviceperson selects "Serial Port" in the center box and chooses a COM port for the serial port. FIG. 6 shows the selection of the COM1 communication port. For a modem connection the serviceperson selects the "Modem" box and enters the phone number for the ultrasound system and a COM port for the modem. Preferably the phone numbers of all of the ultrasound systems for which the serviceperson is responsible are downloaded to the laptop computer and may be selected from the phone number list accessible by the arrow button to the right of the phone number line. Phone numbers dialed by the serviceperson are also saved on the laptop computer. For a network connection to the ultrasound system the serviceperson selects "Network" and enters the IP address or host name for the ultrasound system. Once the desired connection has been selected the serviceperson clicks the Connect button and the diagnostic laptop computer is automatically connected to the ultrasound system.

Figure 7:
FIG. 7 illustrates a banner which may be displayed on the ultrasound system display during remote diagnosis of the ultrasound system.
Figure 8:
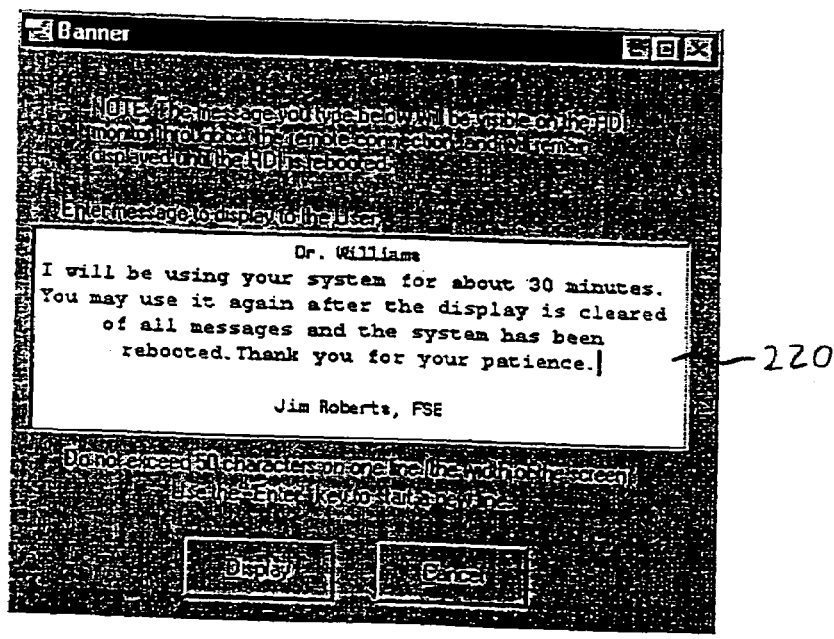
FIG. 8 illustrates the creation of a custom banner or notice to be displayed on the ultrasound system display.

When the laptop computer is remotely connected to the ultrasound system a Diagnostics Mode banner is usually displayed on the display of the ultrasound system to notify the user that the ultrasound system is being serviced. A typical notice banner is shown in FIG. 7. The banner message may be downloaded to the ultrasound system from the laptop computer or a banner utility may be resident in the ultrasound diagnostics software 28 on the ultrasound system and called up for display of resident or remotely downloaded custom messages when remote diagnosis is in progress. The serviceperson has the option of creating custom banners for display on the ultrasound system display. By clicking the Banner button 144 the serviceperson is presented with the custom banner screen shown in FIG. 8. This screen has a window 220 in which the serviceperson can compose a custom message. When the Display button of the banner screen is clicked the custom banner message is transmitted and displayed on the ultrasound system display.

When the laptop computer is connected to the ultrasound system the serviceperson can control certain operating features of the ultrasound system. One important control function is to reboot the ultrasound system, which is done from the laptop computer by clicking the Reboot button 130. This button is usually used at the conclusion of the diagnostic procedure to finish the installation of new software or to place the ultrasound system in its initial operating condition. In the constructed embodiment rebooting will erase any banners previously displayed on the ultrasound system display.

One of the first procedures generally performed by the serviceperson is to transfer diagnostic data on the ultrasound system to the laptop computer. This is done by clicking button 132 on the taskbar. The diagnostic data which is downloaded can include any diagnostic data stored on or produced by the ultrasound systems such as error logs, system options and configuration, test results logs, and network connection information. In a constructed embodiment clicking the Transfer Diagnostics Data button 132 will bring up a file selector screen on which the diagnostic data can be viewed. The file selector can also be configured to access and present a directory of ultrasound system files from which the serviceperson can select the diagnostic data file or files to be downloaded to the laptop computer.

Figure 9:
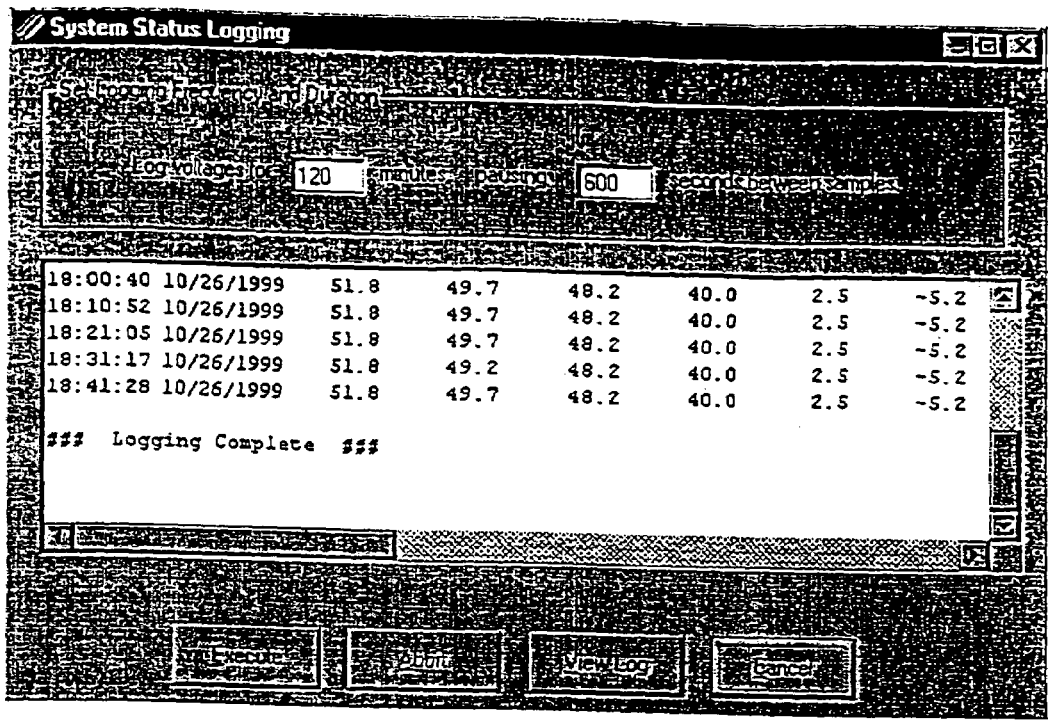
FIG. 9 illustrates the performance of a test of the temperatures and voltages of an ultrasound system.

The Tests button 134 is clicked to cause the ultrasound system to perform certain diagnostic tests and return the results of the tests to the laptop computer. These include high level tests which comprehensively test the ultrasound system from its probe through to its display in different modes of operation. Low level tests can also be invoked, such as those which only exercise specific modules, subsystems, or even specific components of the ultrasound system. Some tests will take a significant amount of time to complete, and can be aborted before completion if desired. One test which has its own button on the toolbar is a test of system voltages and temperatures. When this button 138 is clicked the serviceperson is presented with a screen of the various voltage and temperature tests. The serviceperson can take an instantaneous measurement of the ultrasound system's voltages and temperatures, or can log temperatures and voltages over time by opening the screen shown in FIG. 9. This screen allows the serviceperson to select the duration of the test (120 minutes in this example) and the time intervals at which measurements are taken (ten minutes in this example.) New measurements are displayed periodically in the display window of the screen while the test is underway until it is completed.

The Utilities button 136 enables the serviceperson to select from a number of utilities for file and disk maintenance, system calibration, and self diagnostics. For example, one utility enables the serviceperson to backup or restore system files which need to be saved, may be missing, or need updating. Another utility of the constructed embodiment is used to calibrate sensitive circuitry in the ultrasound system such as the continuous-wave Doppler signal path. The self diagnostics routines stored in ultrasound diagnostics 28 of the ultrasound system can also be selected and invoked from the Utilities button, such as one that exercises the video display on the ultrasound system. The downloading of new software files from a remote location is described in the aforementioned '323 patent.

The Network Files and Status button 140 is used to manage connectivity files on the ultrasound system or determine if a device such as a storage or print device is properly connected to the ultrasound system by way of a network connection. The button 140 can be used to download the host table and device table files from the ultrasound system to the laptop computer, where they can be edited and transferred back to the ultrasound system to effect changes in the network connections of the ultrasound system.

The Transfer and View Images button 142 is used to download images from the ultrasound system to the laptop computer. The entire ultrasound display screen can be transferred, or just the diagnostic ultrasound image can be accessed and downloaded. The remote accessing of ultrasound images is more fully described in the above-mentioned '823 patent.

Figures 10, 11:
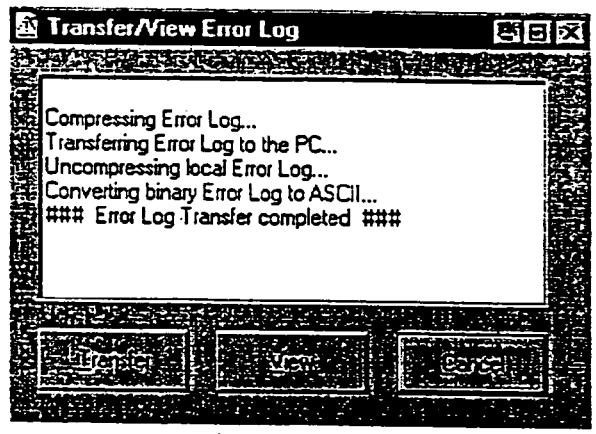
FIG. 10 illustrates a display screen for transmitting an ultrasound system error log to a diagnostics computer.
FIG. 11 illustrates an error log browser.

Clicking the Error Log button 146 will transfer the error log of the ultrasound system to the laptop computer for viewing. The error log is compressed by the ultrasound diagnostics software 28, transferred to the laptop computer, uncompressed and, if necessary, converted to ASCII text. As these operations are underway the transfer/view error log screen shown in FIG. 10 is displayed on the laptop computer to keep the serviceperson apprised of the status of the transfer. In an illustrated embodiment the error log is viewed on an error log browser as shown in FIG. 11, but may also be viewed on a text editor. The constructed embodiment is capable of downloading up to 800 logged errors, including informational error messages. Each logged error event also includes the twenty-five user events (user keystrokes and setting changes) which preceded the error event and, if desired, which succeed the error event. These surrounding user events help define the operating conditions under which the error event arose. The example of FIG. 11 illustrates six user events followed by four italicized informational message lines. These are followed by three error event lines. This information is useful to the serviceperson when diagnosing the error events, and is particularly useful to the ultrasound system designers and manufacturer when modifying the ultrasound system design and software to eliminate potential error conditions, as it provides a fuller understanding of the context of the error conditions. In the constructed embodiment downloaded error logs are automatically saved on the laptop computer for subsequent transfer to the central diagnostics center 120 as described below.

Figure 12:
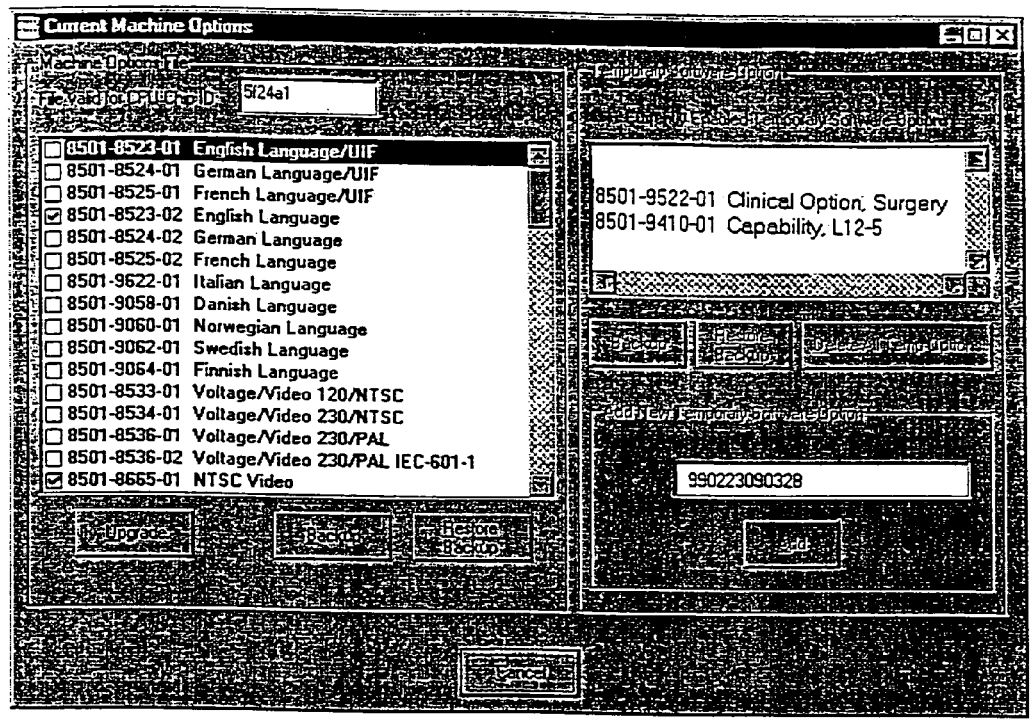
FIG. 12 illustrates a display screen for viewing and changing the capabilities of an ultrasound system.

The Machine Options Files button 148 allows the serviceperson to view and change the ultrasound system's current hardware and software options and temporary software features. When this button is clicked the current machine options screen is displayed as shown in FIG. 12. The window on the left side of the screen shows checkmarks next to the options which are currently active on the ultrasound system. The window on the upper right side of the display shows software-controlled options which are temporarily enabled. This capability is used when the ultrasound system owner wants to try a function for which his or her ultrasound system is not currently enabled. The owner may want to try a new option before purchasing it, for instance. The temporarily enabled options may have been installed in the ultrasound system when it was built, but not activated because the owner did not want the options at the time the ultrasound system was delivered from the factory. Alternatively, a temporarily enabled option may be downloaded to the ultrasound system after the ultrasound system is installed at the owner's location. In a constructed embodiment both resident options and newly downloaded options may be activated for a predetermined period of time by downloading and entering an alphanumeric "key" of characters, numbers, letters, or a combination thereof in the ultrasound system, such as that shown in the window in the lower right side of the display screen of FIG. 12. The numeric key defines both the option to be activated and the period it is to remain active, and is specific to a certain ultrasound system. Generally the numeric key is transmitted to the serviceperson from the manufacturer when the ultrasound system owner orders a new feature for his or her ultrasound system, either for temporary trial or permanent installation. The numeric key is only issued after the manufacturer has ascertained that the ultrasound system can be upgraded with the desired feature, and that the software for the feature is either resident (but inactive) on the ultrasound system or can be downloaded to the ultrasound system by the serviceperson. The new feature is generally fully operational after the ultrasound system has been rebooted.

Clicking the Hardware Configuration button 150 will download the ultrasound system's installed hardware and firmware configuration data and, if desired, the operating system level of the ultrasound system. Further details on remotely accessing ultrasound system configuration files is found in the aforementioned '323 patent.

The Corrupted Files button 152 is used to delete and reset files in the ultrasound system to their factory default settings. For example, the ultrasound system may have user variable files which will retain certain user preferences such as the operator's preferred system setups for certain diagnostic procedures. Since these files can undergo regular modification by the user, it is possible that the files can become faulty or corrupted over time from constant use. When the user first modifies one of these files, the original (default) file is automatically stored by the ultrasound system and a copy of the file is used for the user-entered modifications. The Corrupted Files button produces a display of all files on the ultrasound system which can be restored to their original operating condition. The serviceperson selects a file and clicks an "Execute" button to delete the undesired file, reboot the ultrasound system, and reinstall the factory default file either from the ultrasound system or from the laptop computer. The status of the reinstalled file is displayed in a text window on the laptop computer.

Figure 13:
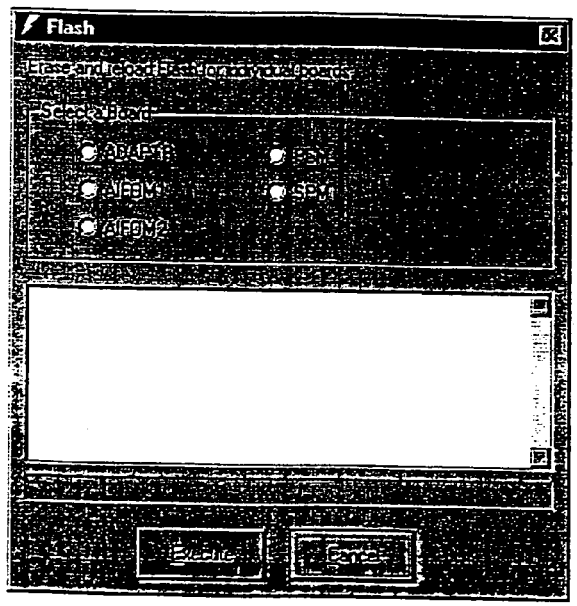
FIG. 13 illustrates a display screen for changing the data of firmware of an ultrasound system.

The Flash button 154 is used to erase and reload (flash) the data of EPROM firmware in the ultrasound system. Clicking the Flash button brings up the flash screen shown in FIG. 13, which gives the serviceperson a selection of ultrasound system printed circuit boards with EPROMs that can be flashed. The serviceperson selects the board or boards to be flashed, then clicks Execute to flash the EPROMs. The EPROMs can be flashed with the original factory default data, or with new data downloaded from the laptop computer.

The Bootup Parameters button 156 displays the ultrasound system's bootup parameters on the laptop computer display. These parameters are invoked by the ultrasound system during bootup (initialization) of the ultrasound system to set the system to its initial operating state. This button and its selections can be used to reset the values of the bootup parameters to their default values or to edit individual parameters for new or different initialization states.

The View Files button 158 can be used to view files which have been transferred from the ultrasound system to the laptop computer. When the View Files button is clicked a directory of all files of the ultrasound system on the laptop computer is displayed in a window on the laptop computer. View Files can also be used to download and view a directory of files on the ultrasound system. Selecting a file from the directory will cause the file to be downloaded to the laptop computer where it can be reviewed and, if desired, edited or replaced.

When the serviceperson is finished servicing the ultrasound system the Disconnect button 94 is clicked to end communication with the ultrasound system. Before ending the connection the serviceperson may leave a banner on the ultrasound system display, informing the ultrasound system user of the service that had been performed. This is particularly useful when the ultrasound system is being serviced after the normal business hours of the facility where the ultrasound system is located. Alternatively, the serviceperson may leave an e-mail on the ultrasound system as explained in U.S. Pat. No. 5,897,498.

The UpLink button 160 is used to send diagnostic data back to the central diagnostics center 120 after the serviceperson is finished servicing the ultrasound system. The UpLink button activates a File Transfer Protocol (FTP) and/or TCP/IP client to transfer diagnostic data from the laptop computer to the central diagnostics center. E-mail macros may also be used to upload the diagnostic data from the laptop computer. In the constructed embodiment the UpLink function is automatically invoked whenever a connection to the central diagnostics center or the Internet is detected. The files which are transferred include the error log files described above which are automatically stored in a directory of upload files. The next time a suitable connection to the diagnostics center or Internet is detected, these files are automatically uploaded to the central diagnostics center. For example, the serviceperson may check his or her e-mail for a list of customers who have requested service. When the serviceperson checks his e-mail, the upload files are automatically sent to the central diagnostics center. Likewise, when the serviceperson connects to the central diagnostics center to download new diagnostic service files, the ultrasound system data stored on the laptop computer is automatically uploaded. The uploading of diagnostic files may proceed in the background on a time shared basis with other communication between the serviceperson and his e-mail box, the manufacturer's Website or intranet, or other central database with which the serviceperson communicates. This automatic capability ensures that all diagnostic data downloaded by all service personnel from ultrasound systems is sent to the central diagnostics center. This data is of considerable importance to the factory, as the full data set can be used to assess root problem causes and to track trends and other statistically relevant events so that potential or newly appearing service conditions can receive a rapid response. Quality manufacturers are not content to simply fix their products, but want to track their tendencies and evolving problem areas so that potential problems can be quickly designed out of current and future products. This capability is enhanced by the assured transmission of all diagnostic data to the central diagnostics center and, ultimately, the designers of the ultrasound systems.

What is claimed is:

1. A distributed ultrasound diagnostics network for diagnosing the functionality of an ultrasound system comprising:
   a plurality of diagnostics computers for diagnosing the functionality of an ultrasound system containing ultrasound system functionality diagnostics software which are operated by servicepersons to download ultrasound system functionality diagnostic information from ultrasound systems; and a central diagnostics location with which said diagnostics computers periodically communicate to transfer said ultrasound system functionality diagnostic information, whereby said central diagnostic location is a repository for ultrasound system repair, maintenance, or quality improvement diagnostic information obtained by said diagnostic computers from a plurality of ultrasound systems.

2. The distributed ultrasound diagnostics network of claim 1, wherein said diagnostics computers comprise portable computers.

3. The distributed ultrasound diagnostics network of claim 2, wherein said portable computers comprise laptop computers.

4. The distributed ultrasound diagnostics network of claim 1, wherein said diagnostics computers download said diagnostic information over a network from locations remote from said ultrasound systems.

5. The distributed ultrasound diagnostics network of claim 4, wherein said diagnostics computers further act to download diagnostic information over a direct connection at the site of said ultrasound systems.

6. The distributed ultrasound diagnostics network of claim 5, wherein said diagnostics computers upload said diagnostic information over a network to said central diagnostics location from locations remote from said central diagnostics location.

7. The distributed ultrasound diagnostics network of claim 1, wherein said ultrasound system diagnostic information comprises information concerning ultrasound system error conditions; and wherein said central diagnostics location operates on said ultrasound system diagnostic information by performing at least one of the following operations:

determining root causes of errors;

statistically analyzing error conditions;

utilizing said diagnostic information to eliminate error conditions from an ultrasound system; and utilizing said diagnostic information to develop a new ultrasound system.

* * * * *